(12) United States Patent
Nadano et al.

(10) Patent No.: US 6,342,640 B1
(45) Date of Patent: Jan. 29, 2002

(54) PROCESS FOR PRODUCING 1,1,3,3-TETRACHLORO-1,3-DIFLUOROACETONE

(75) Inventors: Ryo Nadano; Yoshihiko Goto, both of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/906,232

(22) Filed: Jul. 17, 2001

(30) Foreign Application Priority Data

Jul. 17, 2000 (JP) .......................................... 12-216490

(51) Int. Cl.[7] .............................................. C07C 45/63
(52) U.S. Cl. ..................................................... 568/394
(58) Field of Search ................................ 568/394, 411, 568/419, 393; 570/168, 166, 206

(56) References Cited

U.S. PATENT DOCUMENTS 6,177,595 B1 * 1/2001 Nadano et al. ............. 568/394

FOREIGN PATENT DOCUMENTS

JP          4036262        2/1992

* cited by examiner

Primary Examiner—Alan Siegel
(74) Attorney, Agent, or Firm—Crowell & Moring LLP

(57) ABSTRACT

The invention relates to a process for producing 1,1,3,3-tetrachloro-1,3-difluoroacetone. This process includes fluorinating hexachloroacetone in a liquid phase by hydrogen fluoride in the presence of a catalyst containing a metal compound. This metal compound can be selected from tin halides, titanium halides, molybdenum halides, tungsten halides, niobium halides, tantalum halides, and iron halides. This process is suitable for producing 1,1,3,3-tetrachloro-1,3-difluoroacetone in an industrial scale.

13 Claims, No Drawings

PROCESS FOR PRODUCING 1,1,3,3-TETRACHLORO-1,3-DIFLUOROACETONE

BACKGROUND OF THE INVENTION

The present invention relates to processes for producing 1,1,3,3-tetrachloro-1,3-difluoroacetone, which is useful as an intermediate for medicines and agricultural chemicals and as a reagent for introducing fluorine-containing groups.

Japanese Patent Publication JP-A-4-36262 discloses that 1,1,3,3-tetrachloro-1,3-difluoroacetone, together with 1,1,1,3,3-pentachloro-3-fluoroacetone, can be obtained by fluorinating hexachloroacetone by hydrogen fluoride in the presence of a catalyst, antimony pentachloride. These two kinds of fluoroacetones can be subjected to a haloform reaction, thereby obtaining a single compound. In other words, this publication does not disclose nor suggest at all a process for selectively producing only 1,1,3,3-tetrachloro-1,3-difluoroacetone.

SUMMARY OF THE INVENTION

It is therefore an object of the present invention to provide a process for producing 1,1,3,3-tetrachloro-1,3-difluoroacetone in an industrial scale with a high selectivity.

According to the present invention, there is provided a process for producing a process for producing 1,1,3,3-tetrachloro-1,3-difluoroacetone. This process comprises fluorinating hexachloroacetone in a liquid phase by hydrogen fluoride in the presence of a catalyst comprising a metal compound.

DESCRIPTION OF THE PREFERRED EMBODIMENTS

It is possible by the process of the invention to obtain 1,1,3,3-tetrachloro-1,3-difluoroacetone in an industrial scale with a high selectivity from the corresponding chlorinated compound (i.e., hexachloroacetone) by using the above-mentioned special catalyst, together with hydrogen fluoride, in a liquid-phase fluorination. In the invention, it is not necessary to use a catalyst (e.g., antimony compound) having much environmental impact.

The fluorination may be conducted by a continuous operation, a batch operation, or a half-batch operation in which only the reaction product (hydrogen chloride) is continuously removed from a reactor. Depending on the manner of the operation, it is optional to modify the reaction condition(s).

The starting material, hexachloroacetone, can be synthesized by a conventional process. For example, there is a known process in which acetone is chlorinated by chlorine in the presence of a catalyst (e.g., light, metal chlorides, acids, and metal organic acid salts).

As stated above, the catalyst used in the invention comprises a metal compound. This metal compound is preferably a compound of a metal selected from tin, titanium, niobium, molybdenum, tungsten, tantalum, and iron. The metal compound to be introduced into a reactor is not limited to have a particular form, since the metal compound during the fluorination is assumed to have a particular form depending on the fluorination conditions of the process.

The metal compound is preferably selected from particular compounds (e.g., halides, oxides, nitrates, sulfates, and carbonates) of the above-mentioned particular metals. Of these, halides (chlorides, bromides and fluorides) are preferable. Of halides, chlorides and fluorides are preferable. It is preferable that the metal of the metal compound has a high-valence that is possible under normal conditions. For example, it is tetravalent for tin, tetravalent for titanium, pentavalent for niobium, pentavalent for molybdenum, pentavalent for tantalum, hexavalent for tungsten, and trivalent for iron.

The tin compound as the catalyst is preferably selected from tin halides, such as tin tetrachloride, tin dichloride, tin tetrafluoride, tin difluoride, tin tetrabromide, tin dibromide, tin tetraiodide, and tin diuodide. Of these, tin tetrahalides are preferable. Furthermore, tin tetrachloride is particularly preferable.

Further examples of the metal compound, except those of the tin compound, are titanium tetrachloride, titanium trichloride, titanium tetrabromide, niobium pentachloride, molybdenum pentachloride, tantalum pentachloride, tantalum pentafluoride, tungsten hexachloride, iron trichloride, and iron trifluoride.

The amount of the metal compound used in the process may be 0.001–0.5 moles, preferably 0.01–0.3 moles, more preferably 0.05–0.15 moles, per mole of hexachloroacetone. If it is less than 0.001 moles, both of conversion of hexachloroacetone and yield of 1,1,3,3-tetrachloro-1,3-difluoroacetone may become too low. If it is greater than 0.5 moles, tarry substances made up of high-boiling-point compounds and/or excessively fluorinated reaction products may be produced too much.

The reaction temperature may be from 50 to 300° C., preferably 100–200° C., more preferably 120–180° C. If it is lower than 50° C., both of conversion of hexachloroacetone and yield of 1,1,3,3-tetrachloro-1,3-difluoroacetone may become too low. If it is higher than 300° C., excessively fluorinated reaction products may be produced too much.

The molar ratio of hydrogen fluoride to hexachloroacetone may be from 2 to 50, preferably 3–30, more preferably 5–15. If it is less than 2, conversion of hexachloroacetone may be too low. Even if it is greater than 50, conversion of hexachloroacetone may not improve further. Furthermore, this may not economically be advantageous from the viewpoint of the recovery of the unreacted hydrogen fluoride.

Pressure needed to conduct the fluorination may vary depending on the reaction temperature, and this pressure is not particularly limited as long as the reaction mixture in the reactor is maintained in the form of liquid. The pressure is preferably from 0.1 to 10.0 MPa, more preferably from 0.5 to 5.0 MPa.

Solvent may be added to the reaction system in order to adjust the reaction rate and to suppress deterioration of the catalyst. Preferable examples of this solvent are 1,3-bistrifluoromethylbenzene and 2,4-dichloro-1-trifluoromethylbenzene, which are hardly further fluorinated or chlorinated.

A reactor used in the invention is preferably made of a material such as Hastelloy, stainless steel, Monel metal or nickel, or a material lined with one of these metals, tetrafluoroethylene resin, chlorotrifluoroethylene resin, vinylidene fluoride resin or PFA resin.

It is possible to conduct the process by the following exemplary batch operation. At first, a suitable reactor resistant to the reaction pressure is charged with hydrogen fluoride, the catalyst (e.g., a metal chloride), and the starting material (hexachloroacetone). Then, the reactor is closed and is gradually heated from outside with stirring. With this, the inside pressure rises as the reaction proceeds. In order to adjust the reaction pressure to a certain predetermined value, hydrogen chloride formed by the reaction is allowed to flow out through a reflux condenser disposed on an upper part of the reactor. The amount of hydrogen chloride flowed out is measured. When the molar ratio of hydrogen chloride to hexachloroacetone reaches 2, the heating of the reactor is terminated, followed by cooling. Then, the inside gas (mainly made up of hydrogen chloride and hydrogen fluoride) of the reactor is purged. An organic matter of the reactor and the remaining hydrogen fluoride may be collected in the form of gas or liquid. This hydrogen fluoride can easily be separated from the organic matter. For example, if the remaining hydrogen fluoride is in a large amount, it is possible to separate the resulting layer of hydrogen fluoride from another layer of the organic matter. Furthermore, the organic matter can be treated with a basic substance or calcium compound (e.g., sodium hydroxide, calcium chloride, and calcium hydroxide) to remove acid components and the catalyst, followed by distillation, thereby obtaining 1,1,3,3-tetrachloro-1,3-difluoroacetone of high purity.

The following nonlimitative example is illustrative of the present invention.

Example 1

A 200-ml autoclave, made of stainless steel (SUS316L) and equipped with a reflux condenser, was charged with 5.9 g of tin tetrachloride and 60 g of hexachloroacetone. Then, 57 g of hydrogen fluoride were introduced, and heating was started. 30 minutes after the start of the reaction, the inside temperature and pressure of the autoclave respectively reached 160° C. and 4.0 MPa. Therefore, it was started to allow hydrogen chloride to flow out of the autoclave through the reflux condenser in order to maintain the inside pressure at 4.0 MPa. Under this condition, the reaction was continued. 9 hr after the start of the reaction, the number of moles of hydrogen chloride purged from the autoclave reached two times that of the starting material (hexachloroacetone) charged. Upon this, heating was stopped, followed by cooling. Then, the reaction liquid was taken out of the autoclave. The organic lower layer was separated from another layer and then washed with sulfuric acid, thereby obtaining 47 g of an organic matter. The obtained organic matter was found by gas chromatography to contain 8.7% of 1,1,3-trichloro-1,3,3-trifluoroacetone, 83.3% of 1,1,3,3-tetrachloro-1,3-difluoroacetone, 5.9% of 1,1,1,3,3-pentachloro-3-fluoroacetone, and others.

Then, 6 g of calcium chloride and 2 g of water were added to the obtained organic matter, followed by reflux for 1 hr. The resulting precipitates were removed by filtration. Then, the organic matter was distilled, thereby obtaining 31 g of an organic matter as a main distillate. This organic matter was found by gas chromatography to contain 6.3% of 1,1,3-trichloro-1,3,3-trifluoroacetone, 92.3% of 1,1,3,3-tetrachloro-1,3-difluoroacetone, 1.3% of 1,1,1,3,3-pentachloro-3-fluoroacetone, and others.

The above-mentioned percentages are areal % obtained in gas chromatography.

The entire disclosure of Japanese Patent Application No. 2000-216490 filed on Jul. 17, 2000, including specification, claims and summary, of which priority is claimed in the present application, is incorporated herein by reference in its entirety.

What is claimed is:

1. A process for producing 1,1,3,3-tetrachloro-1,3-difluoroacetone, said process comprising fluorinating hexachloroacetone in a liquid phase by hydrogen fluoride in the presence of a catalyst comprising a metal compound.

2. A process according to claim 1, wherein said metal compound comprises a metal selected from the group consisting of tin, titanium, niobium, molybdenum, tungsten, tantalum and iron.

3. A process according to claim 2, wherein said metal compound is selected from the group consisting of halides, oxides, nitrates, sulfates, and carbonates.

4. A process according to claim 3, wherein said halides are chlorides, bromides and fluorides.

5. A process according to claim 4, wherein said halides are chlorides and fluorides.

6. A process according to claim 3, wherein said metal compound is a tin halide.

7. A process according to claim 6, wherein said tin halide is selected from the group consisting of tin tetrachloride, tin dichloride, tin tetrafluoride, tin difluoride, tin tetrabromide, tin dibromide, tin tetraiodide, and tin diiodide.

8. A process according to claim 6, wherein said tin halide is a tin tetrahalide.

9. A process according to claim 8, wherein said tin tetrahalide is tin tetrachloride.

10. A process according to claim 3, wherein said metal compound is selected from the group consisting of titanium tetrachloride, titanium trichloride, titanium tetrabromide, niobium pentachloride, molybdenum pentachloride, tantalum pentachloride, tantalum pentafluoride, tungsten hexachloride, iron trichloride, and iron trifluoride.

11. A process according to claim 1, wherein said fluorinating is conducted at a temperature of 50–300° C. under a pressure of 0.1–10.0 MPa.

12. A process according to claim 1, wherein said metal compound is in an amount of 0.001–0.5 moles per mole of said hexachloroacetone.

13. A process according to claim 1, wherein said hydrogen fluoride is in an amount of 2–50 moles per mole of said hexachloroacetone.

* * * * *